(12) United States Patent
Fukumoto

(10) Patent No.: US 7,960,308 B2
(45) Date of Patent: Jun. 14, 2011

(54) OXIDE CATALYST, PROCESS FOR PRODUCING ACROLEIN OR ACRYLIC ACID AND PROCESS FOR PRODUCING WATER ABSORBENT RESIN

(75) Inventor: Naohiro Fukumoto, Aioi (JP)

(73) Assignee: Nippon Shokubai Co., Ltd., Osaka (JP)

( * ) Notice: Subject to any disclaimer, the term of this patent is extended or adjusted under 35 U.S.C. 154(b) by 447 days.

(21) Appl. No.: 12/078,299

(22) Filed: Mar. 28, 2008

(65) Prior Publication Data

US 2008/0242815 A1 Oct. 2, 2008

(30) Foreign Application Priority Data

Mar. 29, 2007 (JP) ................... 2007-086628
Nov. 13, 2007 (JP) ................... 2007-294353

(51) Int. Cl.
*B01J 29/06* (2006.01)
*B01J 21/00* (2006.01)
*B01J 29/04* (2006.01)
*B01J 27/228* (2006.01)
*B01J 27/182* (2006.01)
*B01J 23/00* (2006.01)

(52) U.S. Cl. ............. 502/300; 502/66; 502/74; 502/87; 502/179; 502/214

(58) Field of Classification Search ............. 502/66, 502/74, 87, 179, 214, 300
See application file for complete search history.

(56) References Cited

U.S. PATENT DOCUMENTS

| 3,801,634 | A | 4/1974 | Krabetz et al. |
| 4,092,354 | A | 5/1978 | Shiraishi et al. |
| 4,442,308 | A | 4/1984 | Arntz et al. |
| 4,521,618 | A | 6/1985 | Arntz et al. |
| 5,198,581 | A | 3/1993 | Kawajiri et al. |
| 5,364,825 | A | 11/1994 | Neumann et al. |
| 5,719,318 | A | 2/1998 | Kawajiri et al. |
| 6,028,220 | A | 2/2000 | Wada et al. |
| 6,563,000 | B1 | 5/2003 | Yunoki et al. |
| 7,022,643 | B2 | 4/2006 | Yunoki et al. |
| 7,161,044 | B2 | 1/2007 | Nakamura et al. |

FOREIGN PATENT DOCUMENTS

| EP | 0 293 859 | 12/1988 |
| EP | 1 192 986 | 4/2002 |
| JP | 53-30688 | 8/1978 |
| JP | 58-930 | 1/1983 |
| JP | 58-3644 | 1/1983 |
| JP | 4-217932 | 8/1992 |
| JP | 7-10802 | 1/1995 |
| JP | 9-241209 | 9/1997 |
| JP | 10-168003 | 6/1998 |
| JP | 2000-336060 | 12/2000 |
| JP | 2004-136267 | 5/2004 |
| JP | 2005-320315 | 11/2005 |
| JP | 2007-229561 | 9/2007 |

OTHER PUBLICATIONS

Partial English translation of Notice of Reasons for Rejection dated Apr. 14, 2009 issued for Japanese Application No. 2007-294353 corresponding to present U.S. application.
European Search Report issued Sep. 15, 2010 in corresponding European Application No. 08005787.
J. Kunert et al., "*Synthesis of Mo/V Mixed Oxide Catalysts Via Crystallisation and Spray Drying—A Novel Approach for Controlled Preparation of Acrolein to Acrylic Acid Catalysts*," Applied Catalysis, (2004) vol. 269, pp. 53-61.

*Primary Examiner* — Taylor Victor Oh
(74) *Attorney, Agent, or Firm* — Wenderoth, Lind & Ponack, L.L.P.

(57) ABSTRACT

The invention provides a process which enables, in preparation of acrolein by catalytic gas-phase oxidation of propylene in the presence of molecular oxygen or a molecular oxygen-containing gas or in preparation of acrylic acid by catalytic gas-phase oxidation of acrolein in the presence of molecular oxygen or a molecular oxygen-containing gas, using single kind of atalyst, to suppress occurrence of localized extraordinarily high temperature spots (hot spots) in the catalyst layer and can stably maintain high acrolein or acrylic acid yield for a long time. The process is characterized by use of an oxide catalyst containing molybdenum as an essential component and having relative standard deviation of its particle size in a range of 0.02 to 0.20.

3 Claims, No Drawings

OXIDE CATALYST, PROCESS FOR PRODUCING ACROLEIN OR ACRYLIC ACID AND PROCESS FOR PRODUCING WATER ABSORBENT RESIN

TECHNICAL FIELD

This invention relates to catalyst for use in producing acrolein by catalytic gas-phase oxidation of propylene or producing acrylic acid by catalytic gas-phase oxidation of acrolein. More specifically, the invention relates to oxide catalyst containing molybdenum as an essential component, which has specific particle size distribution. The invention also relates to a process for producing acrolein or acrylic acid, using the catalysts, and to a process for producing water-absorbent resin, using so produced acrylic acid.

BACKGROUND ART

Acrolein has been industrially widely used as a starting material for acrylic acid and the like, and acrylic acid, as starting material for water-absorbent resin. Generally practiced production processes of acrolein or acrylic acid comprise catalytic gas-phase oxidation of propylene, or catalytic gas-phase oxidation of acrolein, using a fixed bed shell-and-tube reactor, in the presence of an oxidation catalyst.

This catalytic gas-phase oxidation reaction is a highly exothermic reaction, and hence locally extraordinarily high temperature spots (hereafter may be referred to as "hot spots") are formed in the catalyst layers. At the hot spots the oxidation reaction progresses excessively, because of the higher temperature than that at the rest of the reaction area, to reduce yield of the object product, i.e., acrolein or acrylic acid. Moreover, because the hot spots are exposed to high temperatures, the catalyst at the spots shows changes in physical and chemical properties within a short period, which leads to notable decrease in its activity or selectivity due to sintering or the like. In particular, when the catalyst contains molybdenum, high temperatures at hot spots accelerate sublimation of the molybdenum to cause changes in the catalyst's composition (ratios among its constituents) and therefore the deterioration extent of the catalyst is large. There is still another problem that this phenomenon is enhanced when the reaction is carried out at high space velocity or high starting gas concentration, i.e., when a high-load reaction is carried out, for improving productivity of acrolein or acrylic acid.

In order to cope with these problems, various improvement means have been proposed for preparing acrolein from propylene, for example, a method comprising filling the reaction tube with plural kinds of catalysts differing in occupation volume, mixing in at least one of the reaction zones an inert substance molding (Patent Reference 1: JP 2005-320315A=U.S. Pat. No. 7,161,044); a method using a supported catalyst, comprising filling the reaction tube with plural kinds of catalysts having different activities which are prepared by varying the supported ratio of catalytically active component on the catalysts and/or calcining temperature, in such a manner that the activity becomes higher from the starting gas-inlet side toward the outlet side (Patent Reference 2: JP Hei 10 (1998)-168003A=U.S. Pat. No. 6,028,200); or a method of filling the reaction tube with plural catalysts in such a manner that the occupation volume of catalyst filled in the reaction tube becomes lower from the starting gas-inlet side toward the outlet side (Patent Reference 3: JP Hei 4 (1992)-217932A=U.S. Pat. No. 5,198,581).

Concerning preparation of acrylic acid from acrolein, various improvements have also been proposed, for example, a method comprising diluting the catalyst at the starting gas-inlet side with an inert substance (Patent Reference 4: JP Sho 53 (1978)-30688B=U.S. Pat. No. 3,801,634); a method using a supported catalyst, comprising filling the reaction tube with the catalyst in which supported ratio of catalytically active component becomes higher from the starting gas-inlet side toward the outlet side (Patent Reference 5: JP Hei 7 (1995)-10802A); a method comprising preparing plural catalysts having different activities by varying the kind and/or amount of alkali metal added to the catalyst, and filling them in the reaction tube in such a manner that the catalytic activity becomes higher from the starting gas-inlet side toward the outlet side (Patent Reference 6: JP 2000-336060A=U.S. Pat. No. 6,563,000); and a method comprising filling the reaction tube in such a manner that the volume of catalyst particles become smaller from the starting gas-inlet side toward the outlet side (Patent Reference 7: JP Hei 9 (1997)-241209A=U.S. Pat. No. 5,719,318).

However, such means as dilution with inactive substance, varying the supported ratio or use of catalysts having different activities reduce the amount of the catalytic component effective for the reaction, which is filled in the reaction tube, to impair productivity of acrylic acid. Preparation of plural catalysts also requires much labor and huge cost, compared to preparation of single kind of catalyst.

Still in addition, while all of above proposals accomplish improvement in suppressing temperature at hot spots to a certain extent, the effect is yet unsatisfactory. That is, it is the current situation that there is still room for improvements in those methods in respect of both catalyst life and yield of acrolein or acrylic acid.

OBJECT OF THE INVENTION

Thus, an object of the present invention is to provide a catalyst which, in preparation of acrolein by catalytic gas-phase oxidation of propylene or preparation of acrylic acid by catalytic gas-phase oxidation of acrolein, can suppress occurrence of localized extraordinarily high temperature spots (hot spots) in the catalyst layers and can give high acrolein or acrylic acid yield stably for a long time.

MEANS OF SOLUTION

We discovered: in a production process of acrolein by catalytic gas-phase oxidation of propylene or that of acrylic acid by catalytic gas-phase oxidation of acrolein, using a fixed bed shell-and-tube reactor, when the catalyst filled in the reactor had a specific particle size distribution, voids between the catalyst particles could be uniformized and enlarged, occurrence of localized extraordinarily high temperature spots (hot spots) in the catalyst layers could be suppressed without reducing productivity of acrolein or acrylic acid, and acrolein or acrylic acid could be stably obtained for a long time. The present invention was whereupon completed.

Accordingly, therefore, this invention provides an oxide catalyst containing molybdenum as an essential component, which is characterized in that the relative standard deviation of its particle size as determined according to the following formula (1):

$$\text{relative standard deviation of particle size} = \quad (1)$$
$$\text{standard deviation of particle size/average particle size}$$
$$\text{wherein the standard deviation of particle size} =$$
$$\sqrt{\frac{N\Sigma Xn^2 - (\Sigma Xn)^2}{N(N-1)}}$$

(N is the number of particles whose size is measured; Xn is the size of each particle in terms of triaxial average diameter which is the average value of diameters measured in three directions of each particle); and the average particle size is the arithmetic mean of particle sizes of N particles is at least 0.02 and no more than 0.20.

The invention also provides a process for preparing acrolein by catalytic gas-phase oxidation of propylene in the presence of molecular oxygen or a molecular oxygen-containing gas or a process for producing acrylic acid by catalytic gas-phase oxidation of acrolein in the presence of molecular oxygen or a molecular oxygen-containing gas, characterized by using the above catalyst. The invention furthermore provides a process for preparing water-absorbent resin, using the acrylic acid which is obtained by the process as the starting material.

EFFECT OF THE INVENTION

The catalyst of the present invention can be favorably used as the catalyst for preparing acrolein or acrylic acid with a fixed bed shell-and-tube reactor, as it suppresses occurrence of localized extraordinarily high temperature spots (hot spots) in the catalyst layers and can stably maintain high acrolein or acrylic acid yield for a long time.

BEST MODE FOR WORKING THE INVENTION

It is satisfactory for the catalyst of the present invention to contain molybdenum as an essential component and have the relative standard deviation in its particle size as determined by the formula (1) within a range of at least 0.02 and no more than 0.20. When the filled amount of the catalytic component per reaction tube is adequately maintained, the catalyst can suppress occurrence of hot spots and enable high-load reaction to maintain high productivity of acrolein or acrylic acid with stability for a long time. Where the relative standard deviation of the catalyst particle size is less than 0.02, i.e., where the catalyst's particle size is uniform, uniform and large voids are present among the particles filled in the reaction tubes. In this case it is possible to suppress occurrence of hot spots, but the amount of the catalytic component filled per reaction tube decreases and it becomes necessary to raise the reaction temperature for achieving a sufficient conversion of the starting material of the reaction. In consequence, productivity of acrolein or acrylic acid decreases due to drop in selectivity for the object product and acceleration in deterioration of the catalyst. On the other hand, where the relative standard deviation of the catalyst's particle size exceeds 0.20, i.e., where the catalyst has a too broad particle size distribution, when it is filled in the reaction tube small particles enter into the voids among large particles and inter-particulate voids are drastically reduced. In consequence, although the amount of the filled catalytic component per reaction tube increases, occurrence of hot spots cannot be suppressed, and productivity of acrolein or acrylic acid drops, due to increase in combustion reaction caused by high temperature and acceleration in deterioration of the catalyst.

In the present invention, shape of the catalyst particles is not necessarily a true sphere, but substantially spherical shape is satisfactory. The particle size is expressed by the average value of diameters measured of three directions per particle (triaxial average diameter). When the number of measured particles is sufficiently large, it is unnecessary to measure all of the particles, but measurements of randomly sampled particles from the whole is sufficient.

The average particle size of the catalyst can be suitably selected according to the inner diameter of the reaction tubes of a fixed bed shell-and-tube reactor. Generally, inner diameter of the reaction tubes used in above reaction is 10-60 mm, and the average particles size of the catalyst is preferably 1-12 mm, in particular, 3-10 mm.

Those oxide catalysts according to the present invention, which are convenient for preparing acrolein by catalytic gas-phase oxidation of propylene with molecular oxygen or a molecular oxygen-containing gas, contain active component represented by the following formula (2):

$$Mo_{12}Bi_aFe_bA_cB_dC_eD_fO_x \qquad (2)$$

(wherein Mo is molybdenum, Bi is bismuth, Fe is iron, A is at least an element selected from cobalt and nickel, B is at least an element selected from alkali metals, alkaline earth metals and thallium, C is at least an element selected from tungsten, silicon, aluminum, zirconium and titanium; D is at least an element selected from phosphorus, tellurium, antimony, tin, cerium, lead, niobium, manganese, arsenic and zinc, and O is oxygen; a, b, c, d, e, f and x are respective atomic ratios of Bi, Fe, A, B, C, D and O, which are, respectively, $0<a\leq10$, $0<b\leq20$, $2\leq c\leq20$, $0<d\leq10$, $0\leq e\leq30$, $0\leq f\leq4$, and x is a numerical value determined by the state of oxidation of respective elements).

Also as the oxide catalysts according to the present invention to be used for preparation of acrylic acid by catalytic gas-phase oxidation of acrolein with molecular oxygen or a molecular oxygen-containing gas, those containing the active component represented by the following formula (3) are preferred:

$$Mo_{12}V_gW_hCu_iE_jF_kG_lH_mO_y \qquad (3)$$

(wherein Mo is molybdenum, V is vanadium, W is tungsten, Cu is copper, E is at least an element selected from cobalt, nickel, iron, lead and bismuth, F is at least an element selected from antimony, niobium and tin, G is at least an element selected from silicon, aluminum, titanium and zirconium, H is at least an element selected from alkali metals, and O is oxygen; g, h, i, j, k, l, m and y are respective atomic ratios of V, W, Cu, E, F, G, H and O, which are, respectively, $2\leq g\leq15$, $0\leq h\leq10$, $0\leq i\leq6$, $0\leq j\leq30$, $0\leq k\leq6$, $0\leq l\leq60$, $0\leq m\leq-6$, and y is a numerical value determined by the state of oxidation of respective elements).

The catalysts according to the present invention may be in the form of molded catalysts formed by molding those catalytically active components as in the above formulae as they are, or in the form of supported catalysts in which the catalytically active components are supported on carriers inert to the reaction. Those catalytically active components as in the above formulae can be prepared from starting materials commonly used in preparation of this type of catalysts, by a method generally used. As the starting materials, for example, oxides, hydroxides, salts such as ammonium salts, nitrates, carbonates, sulfates, organic acid salts and the like; aqueous solutions thereof, sols thereof, compounds containing plural kinds of the elements or the like can be used.

For preparation of a molded catalyst, those starting materials are successively added to a solvent like water to form an aqueous solution, suspension or slurry, and drying the resulting aqueous solution, suspension or slurry containing the catalytic components by a suitable method. As the drying method, for example, evaporation to dryness can be done, or dry powder may be formed using spray dryer, drum dryer or the like, or a box-type or tunnel-type dryer may be used in which heating is conducted in a gaseous current to provide dry blocks or flakes. It is also possible to use a vacuum dryer to effect drying under reduced pressure, to provide dry blocks or powder. Thus obtained dry product is sent to a molding step, after going through such a step as pulverization or classification, where necessary, to obtain a powder of adequate particle size. The dry product may also be calcined before the molding step, where necessary. Molding method of the catalyst is subject to no particular limitation, so long as it can mold substantially spherical catalyst particles. Known methods, for example, molding with Marumerizer™ and the like can be used. Whereupon obtained molded product is dried, where necessary, and calcined at temperatures ranging 300-600° C., preferably 350-500° C., for about 1-10 hours to provide an oxide catalyst.

Any methods which enable to uniformly support above catalytically active component on a carrier are effective for preparation of supported catalyst. For example, an aqueous solution, suspension or slurry which contains the catalytically active component as expressed by either of the above formulae is dried, pulverized and optionally calcined, and carried using a rotatory drum-type coating apparatus, tumbling granulator, rotating and straggling type mixer or the like, adding a binder such as an alcohol or water, where necessary. It is also effective to impregnate a carrier with an aqueous solution, suspension or slurry which contains the catalytically active component as expressed by either of the above formulae. The carrier thus supporting the catalytically active component is dried, where necessary, and calcined at temperatures ranging 300-600° C., preferably 350-500° C., for about 1-10 hours to provide a supported oxide catalyst.

As the carrier for the supported catalyst, any of those used for various known catalysts, in particular, for propylene-oxidation reaction catalysts or acrolein-oxidation reaction catalysts, are useful. They are preferably substantially spherical. More specifically, silica, alumina, silica-alumina, silicon carbide, silicon nitride, titanium oxide, zirconium oxide and the like can be used, among which alumina and silica-alumina are preferred. The carrier may be those commercially available, while they can be prepared from starting materials containing those constituent elements.

Preferred particle size of the carrier is 1-12 mm, in particular, 3-10 mm. A carrier whose particle size is within the above-specified range and whose relative standard deviation as determined according to the formula (1) is at least 0.02 and no more than 0.20 is particularly preferred, because its use allows easy preparation of a catalyst with relatively uniform content of active component, having a relative standard deviation of its particle size falling within the range specified by this invention. While a carrier satisfying the above conditions can be directly prepared, it is also possible to screen the carrier after preparation to sift out the particles satisfying the above conditions.

Molded catalyst can similarly be directly prepared to satisfy the condition of the formula (1), or the prepared catalyst itself may be sieved to sift out the catalyst particles satisfying the condition of the formula (1).

To those catalysts of the present invention, molding assistant such as ammonium nitrate, cellulose or the like, or reinforcing agent such as glass fiber, ceramic fiber or the like can be added, besides the catalytically active components.

The present invention is effectively applicable to all catalysts comprising the specified catalytically active components, in particular, to the catalysts of high activity, with still higher effect. The invention is very effective, furthermore, when high-load reaction is carried out to improve productivity of acrolein or acrylic acid.

In the occasions of producing acrolein by catalytic gas-phase oxidation of propylene or producing acrylic acid by catalytic gas-phase oxidation of acrolein, using fixed bed shell-and-tube reactor in the presence of a catalyst of the present invention, it is unnecessary to fill the tubes with the catalyst in divided, plural layers, but by simply filling the tubes with single kind of the catalyst, occurrence of hot spots can be suppressed to enable to keep high acrolein or acrylic acid productivity even in the reactions under high space velocity or high starting gas concentration. Needless to say, adoption of such a method as filling the tubes with divided plural layers of the catalyst and diluting a part of the catalyst with an inert substance or combined use of plural kinds of oxidation catalysts prepared by varying the components, preparation means, calcining conditions or the like, does not impair the effect of the present invention. A method of filling the reaction tubes with divided, plural catalyst layers of plural kinds of oxidation catalysts having different occupation volumes may also be used, in which occasion the oxidation catalyst in each of the divided layers is adjusted to have a relative standard deviation within the range specified by the present invention.

Reaction conditions for producing acrolein from propylene according to the present invention are subject to no particular limitation, and the reaction is operable under any conditions generally used for this kind of reaction. For example, as the starting gas a gaseous mixture composed of 1-15 vol %, preferably 4-12 vol %, of propylene, 0.5-25 vol %, preferably 2-20 vol % of molecular oxygen, 0-30 vol %, preferably 0-25 vol %, of steam and the balance of inert gas such as nitrogen, is used, which is contacted with the oxidation catalyst at 200-400° C., under a pressure of 0.1-1.0 MPa and at a space velocity of 300-5,000 $h^{-1}$ (STP).

Similarly, reaction conditions for producing acrylic acid from acrolein are subject to no particular limitation, and the reaction is operable under any conditions generally used for this kind of reaction. For example, as the starting gas a gaseous mixture composed of 1-15 vol %, preferably 4-12 vol %, of acrolein, 0.5-25 vol %, preferably 2-20 vol % of molecular oxygen, 0-30 vol %, preferably 0-25 vol % of steam and the balance of an inert gas such as nitrogen can be used, which is contacted with the oxidation catalyst at temperatures ranging 200-400° C., under a pressure of 0.1-1.0 MPa and at a space velocity of 300-5,000 $h^{-1}$ (STP). Obviously the acrolein-containing gas obtained by above catalytic gas-phase oxidation of propylene can be used as an acrolein-containing gas in this reaction. In such occasions, well known methods may be applied such as using two reactors of the first reactor filled with a catalyst for oxidizing propylene and the second reactor filled with a catalyst for oxidizing acrolein, and introducing the acrolein-containing gas from the first reactor, recycling gas, oxygen, or an inert gas such as nitrogen or steam into the second reactor to further oxidize the acrolein to produce acrylic acid; or using a reactor which is divided into two reaction zones, filling one of the reaction zones with propylene-oxidizing catalyst and the other reaction zone, with acrolein-oxidizing catalyst, to produce acrylic acid from propylene. Also mixed gas containing acrolein, which is obtained by using propane as the starting material, can be used. Air or oxygen or the like may be added to such gaseous mixtures where necessary.

An acrylic acid-containing gas as obtained by such catalytic gas-phase oxidation is converted to an acrylic acid-containing liquid by absorbing it into a solvent such as water or high-boiling hydrophilic organic solvent or the like, or by processing it by known method such as direct condensation. So obtained acrylic acid-containing liquid is purified by known extraction, distillation or crystallization method, to provide pure acrylic acid. A water-absorbent resin can be obtained by using the resulting purified acrylic acid and/or a salt thereof as the base monomer (preferably at least 70 mol %, in particular, at least 90 mol %), adding thereto about 0.001-5 mol % of a crosslinking agent and about 0.001-2 mol % of a radical polymerization initiator both based on the acrylic acid to cause crosslinking polymerization, drying the resulting polymer and pulverizing the same.

Water-absorbent resin is a water-swellable and water-insoluble polyacrylic acid having crosslinked structure, which absorbs at least 3 times, preferably 10-1000 times, its own weight of pure water or physiological saline to produce a water-insoluble hydrogel preferably containing not more than 25 mass %, in particular, not more than 10 mass %, of water-soluble component. Specific examples of such water-absorbent resin or measurement methods of their physical properties are described in, for example, U.S. Pat. Nos. 6,107, 358, 6,174,978 and 6,241,928.

EXAMPLES

Hereinafter the present invention is explained more specifically, referring to working Examples, it being understood that the invention is not limited to these Examples only. In the following, "mass parts" may be simply written as "parts" for convenience. The propylene conversion, acrolein conversion, acrolein yield and acrylic acid yield given in the Examples are defined as follows:

$$\text{propylene conversion}(\text{mol}\%) = \frac{\left(\begin{array}{c}\text{number of mols of}\\ \text{reacted propylene}\end{array}\right)}{\left(\begin{array}{c}\text{number of mols of}\\ \text{supplied propylene}\end{array}\right)} \times 100$$

$$\text{acrolein yield}(\text{mol}\%) = \frac{\left(\begin{array}{c}\text{number of mols of}\\ \text{formed acrolein}\end{array}\right)}{\left(\begin{array}{c}\text{number of mols of}\\ \text{supplied propylene}\end{array}\right)} \times 100$$

$$\text{acrolein conversion}(\text{mol}\%) = \frac{\left(\begin{array}{c}\text{number of mols of}\\ \text{reacted acrolein}\end{array}\right)}{\left(\begin{array}{c}\text{number of mols of}\\ \text{supplied acrolein}\end{array}\right)} \times 100$$

$$\text{acrylic acid yield}(\text{mol}\%) = \frac{\left(\begin{array}{c}\text{number of mols of}\\ \text{formed acrylic acid}\end{array}\right)}{\left(\begin{array}{c}\text{number of mols of}\\ \text{supplied acrolein}\end{array}\right)} \times 100$$

Example 1

-Preparation of Carrier-

Ninety (90) parts of α-alumina powder of 2-10 μm in average particle size and 5 parts of methyl cellulose as an organic binder were thrown into a kneader and mixed thoroughly. Then 3 parts (in terms of $Al_2O_3$ content) of alumina sol of 2-20 nm in average particle size and 7 parts (in terms of $SiO_2$ content) of colloidal silica of 2-20 nm in average particle size were added to the mixture. Further pouring water into the kneader and thoroughly mixing them, an alumina mixture to which silica was added was obtained. The mixture was extrusion molded to form cylindrical molded article of about 5.5 mm in diameter and about 3.0-7.0 mm in length (average 5.5 mm), which was successively granulated until spherical particles were formed. Drying the same, the particles were calcined at 1400° C. for 2 hours, followed by sifting out with a sieve of a mesh size not more than 5.6 mm but not less than 4.0 mm. One-hundred $(100)_g$ of thus obtained carrier was sampled and measured of particle size. The average particle size was 5.00 mm, the standard deviation in the formula (1) was 0.25, and relative standard deviation was 0.05.

-Preparation of Catalyst-

In 2,000 parts of distilled water, 350 parts of ammonium molybdate was dissolved by heating under stirring (liquid A). Separately, 154 parts of cobalt nitrate and 144 parts of nickel nitrate were dissolved in 500 parts of distilled water (liquid B). Further separately 73.4 parts of ferric nitrate and 120 parts of bismuth nitrate were dissolved in 350 parts of distilled water which had been rendered acidic by addition of 15 parts of conc. nitric acid (65 mass %) (liquid C). These nitrate solutions (liquids B and C) were dropped into liquid A. Successively, 993 parts of 20 mass % silica sol and 0.84 part of potassium nitrate were added. The resulting suspension was heated, stirred and vaporized, and the dry product was further dried at 200° C. and pulverized to a size not greater than 150 μm, to provide a catalyst powder. Into a centrifugal fluidized coating apparatus, 1750 parts of the above carrier was thrown, and then the catalyst powder was thrown thereinto while passing through 90° C. hot air current, together with a 35 mass % aqueous ammonium nitrate solution serving as a binder, to have the carrier support the catalyst component. Thereafter the supported catalyst was given a heat treatment at 470° C. for 6 hours in an atmosphere of air to provide an oxide catalyst. The composition of the metallic elements constituting the catalytically active component excepting oxygen was as follows:

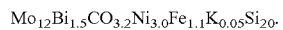

$Mo_{12}Bi_{1.5}CO_{3.2}Ni_{3.0}Fe_{1.1}K_{0.05}Si_{20}$.

The carriage ratio of this oxide catalyst as calculated by the following equation was about 30 mass %.

$$\text{supported ratio}(\text{mol}\%) = \frac{(\text{mass of oxide catalyst} - \text{mass of carrier})}{(\text{mass of carrier})} \times 100$$

The results of sampling 100 g of the oxide catalyst and measuring the particle sizes were as follows: average particle size: 5.22 mm, standard deviation: 0.31, and relative standard deviation: 0.06.

-Reaction-

The oxide catalyst was filled in a steel reactor of 25 mm in inner diameter and 3,000 mm in length, to a filled catalyst layer length of 2,000 mm. At the reactant gas-inlet side of the catalyst layer, inert alumina balls of 5 mm in average particle size was filled to a length of 200 mm as a preheating layer. Into the reactor a gaseous mixture composed of 7.5 vol % of propylene, 64 vol % of air, 21 vol % of steam and the balance of inert gas such as nitrogen was introduced, and the reaction was carried out at a space velocity to the oxide catalyst of 1700 $h^{-1}$ (STP). The performances at the initial stage of the reaction and that after 2,000 hours of the reaction were as shown in Table 1.

Example 2

Example 1 was repeated except that the carrier was sifted out with a sieve of the mesh size not more than 5.6 mm and not less than 3.4 mm at the time of the carrier preparation. The results were as shown in Table 1. The average particle size of the carrier was 4.82 mm, standard deviation was 0.67, and relative standard deviation was 0.14. The oxide catalyst obtained had an average particle size of 5.12 mm, standard deviation of 0.56 and relative standard deviation of 0.11.

Comparative Example 1

Example 1 was repeated except that the carrier was sifted out with a sieve of the mesh size not more than 5.6 mm and not less than 2.4 mm at the time of the carrier preparation. The results were as shown in Table 1. The carrier had an average particle size of 4.99 mm, standard deviation of 1.05 and relative standard deviation of 0.21. The oxide catalyst as obtained had an average particle size of 5.17 mm, standard deviation of 1.19 and relative standard deviation of 0.23.

Comparative Example 2

Example 1 was repeated except that the carrier was sifted out with a sieve with the mesh size not more than 5.6 mm and not less than 4.6 mm at the time of the carrier preparation. The results were as shown in Table 1. The carrier had an average particle size of 5.00 mm, standard deviation of 0.05 and relative standard deviation of 0.01. The oxide catalyst as obtained had an average particle size of 5.20 mm, standard deviation of 0.05 and relative standard deviation of 0.01.

Example 3

-Preparation of Catalyst-

Into 4,000 parts of distilled water, 513 parts of ammonium paramolybdate, 170 parts of ammonium metavanadate and 78.5 parts of ammonium paratungstate were dissolved under heating and stirring. Separately, 146 parts of copper nitrate was dissolved in 200 parts of distilled water under heating and stirring. Thus obtained two aqueous solutions were mixed, and into which further 48.4 parts of titanium oxide and 35.3 parts of antimony trioxide were added to form a suspension. The suspension was put in a porcelain evaporator on a hot water bath, and into which 1750 parts of the carrier as prepared in Example 1 was added. The system was evaporated to dry solid under stirring, to deposit the catalytic component on the carrier. Thus formed supported catalyst was taken out and heat-treated at 400° C. for 6 hours in an atmosphere of air to provide an oxide catalyst. The composition of the metallic elements constituting the catalytically active component excepting oxygen was as follows:

$Mo_{12}V_6W_{1.2}Cu_{2.5}Sb_1Ti_{2.5}$.

The supported ratio of this oxide catalyst was about 30 mass %.

The average particle size of the oxide catalyst was 5.16 mm, standard deviation was 0.21, and the relative standard deviation was 0.04.

-Reaction-

The oxide catalyst was filled in a steel reaction tube of 25 mm in inner diameter and 3,000 mm in length, to a filled catalyst layer length of 2,000 mm. At the reactant gas-inlet side of the catalyst layer, inert alumina balls of 5 mm in average particle size was filled to a length of 200 mm as a preheating layer. Into the reaction tube a gaseous mixture composed of 7 vol % of acrolein, 35 vol % of air, 15 vol % of steam and the balance of inert gas such as nitrogen was introduced, and the reaction was carried out at a space velocity to the oxide catalyst of 1500 $hr^{-1}$ (STP). The performances at the initial stage of the reaction and that after 2,000 hours of the reaction were as shown in Table 2.

Example 4

The catalyst preparation and the reaction were carried out in the same manner with Example 3, except that the carrier as obtained in Example 2 was used as the carrier. The results were as shown in Table 2. The oxide catalyst had an average particle size of 5.16 mm, standard deviation of 0.67 and relative standard deviation of 0.13.

TABLE 1

|  | Carrier | | Catalyst | | | | | | |
|---|---|---|---|---|---|---|---|---|---|
|  | Average particle size (mm) | Relative standard deviation | Average particle size (mm) | Relative standard deviation | Operation Time (hr) | Reaction Temp. (° C.) | Hot Spot Temp. (° C.) | Propylene Conversion (mol %) | Acrolein Yield (mol %) |
| Example 1 | 5.00 | 0.05 | 5.22 | 0.06 | initial stage | 313 | 60 | 98.5 | 83.1 |
|  |  |  |  |  | 2000 | 314 | 61 | 98.5 | 83.2 |
| Example 2 | 4.82 | 0.14 | 5.12 | 0.11 | initial stage | 315 | 62 | 98.6 | 82.9 |
|  |  |  |  |  | 2000 | 316 | 60 | 98.5 | 82.9 |
| Comparative Example 1 | 4.99 | 0.21 | 5.17 | 0.23 | initial stage | 305 | 92 | 99.1 | 76.1 |
|  |  |  |  |  | 2000 | 313 | 91 | 98.9 | 75.6 |
| Comparative Example 2 | 5.00 | 0.01 | 5.20 | 0.01 | initial stage | 324 | 57 | 98.2 | 77.3 |
|  |  |  |  |  | 2000 | 327 | 58 | 97.5 | 76.3 |

Comparative Example 3

The catalyst preparation and reaction were carried out in the same manner with Example 3, except that the carrier as obtained in Comparative Example 1 was used as the carrier. The results were as shown in Table 2. The oxide catalyst had an average particle size of 5.16 mm, standard deviation of 1.08 and relative standard deviation of 0.21.

Comparative Example 4

The catalyst preparation and the reaction were carried out in the same manner with Example 3, except that the carrier as obtained in Comparative Example 2 was used as the carrier. The results were as shown in Table 2. The oxide catalyst had an average particle size of 5.19 mm, standard deviation of 0.07 and relative standard deviation of 0.01.

Example 5

The catalyst as obtained in Comparative Example 3 was sifted out with a sieve of a mesh size not more than 5.6 mm and not less than 3.4 mm. Otherwise, the catalyst preparation and the reaction were carried out in the same manner with Comparative Example 3. The oxide catalyst after the sifting had an average particle size of 5.13 mm, standard deviation of 0.77 and relative standard deviation of 0.15. The results were as shown in Table 2.

Example 6

-Preparation of Carrier-

Seventy-five (75) parts of α-alumina powder of 2-10 μm in average particle size and 5 parts of methyl cellulose as an organic binder were thrown into a kneader and mixed thoroughly. Then 8 parts (in terms of $Al_2O_3$ content) of alumina sol of 2-20 nm in average particle size and 17 parts (in terms of $SiO_2$ content) of colloidal silica of 2-20 nm in average particle size were added to the mixture. Further pouring water into the kneader and mixing thoroughly, a silica-added alumina mixture was obtained. The mixture was extrusion molded to form cylindrical molded article of about 8.5 mm in diameter and about 6.0-10.0 mm in length (average 8.5 mm), which was successively granulated until spherical particles were obtained. Drying the same, the particles were calcined at 1400° C. for 2 hours, followed by sifting out with a sieve of a mesh size not more than 8.5 mm and not less than 7.2 mm. Thus obtained carrier had an average particle size of 8.00 mm, standard deviation of 0.32 and relative standard deviation of 0.04.

-Preparation of Catalyst-

In 4,000 parts of distilled water, 530 parts of ammonium paramolybdate, 87.7 parts of ammonium metavanadate and 74.2 parts of ammonium paratungstate were dissolved under heating and stirring. Separately, 72.4 parts of copper nitrate and 14.5 parts of cobalt nitrate were dissolved in 200 parts of distilled water under heating and stirring. Thus obtained two aqueous solutions were mixed, and into which further 29.1 parts of antimony trioxide was added to provide a suspension. The suspension was put in a porcelain evaporator on a hot water bath, and into which 1750 parts of above carrier was added. The system was evaporated to dry solid under stirring, to deposit the catalytic component on the carrier. Thus formed supported catalyst was taken out and given a heat-treatment at 400° C. for 6 hours in an atmosphere of air, to provide an oxide catalyst. The supported ratio of this oxide catalyst was about 30 mass %, and the composition of the metallic elements constituting the catalytically active component excepting oxygen was as follows:

$$Mo_{12}V_3W_{1.1}Cu_{1.2}Sb_{0.8}Co_{0.2}.$$

The oxide catalyst had an average particle size of 8.50 mm, standard deviation of 0.34 and relative standard deviation of 0.04.

-Reaction-

Thus obtained oxide catalyst was used in a reaction in the same manner with Example 3. The results were as shown in Table 2.

Example 7

In 4,000 parts of distilled water, 530 parts of ammonium paramolybdate, 87.7 parts of ammonium metavanadate and 74.2 parts of ammonium paratungstate were dissolved under heating and stirring. Separately, 72.4 parts of copper nitrate and 14.5 parts of cobalt nitrate were dissolved in 200 parts of distilled water under heating and stirring. Thus obtained two aqueous solutions were mixed, and into which further 29.1 parts of antimony trioxide was added to provide a suspension. This suspension was dried with a spray dryer. The resulting granular powder was calcined at 390° C. for about 5 hours. In that occasion a thermometer was inserted in the granular powder, and the oven temperature was raised in controlled manner so as to avoid rapid temperature rise. The calcined granular powder was pulverized to a size not greater than 150 μm to provide a catalyst powder. Into a centrifugal fluidized coating apparatus, 1750 parts of the carrier as obtained in Example 6 was thrown, and then the catalyst powder was thrown thereinto through 90° C. hot air current, together with 20 mass % of aqueous glycerine solution as a binder, to be supported on the carrier. Subjecting the product to a heat-treatment at 400° C. for 6 hours in an atmosphere of air, an oxide catalyst was obtained. The supported ratio of this oxide catalyst was about 30 mass %, and the composition of the metallic elements constituting the catalytically active component excepting oxygen was as follows:

$$Mo_{12}V_3W_{1.1}Cu_{1.2}Sb_{0.8}Co_{0.2}.$$

The oxide catalyst had an average particle size of 8.95 mm, standard deviation of 0.36 and relative standard deviation of 0.04.

-Reaction-

Using the catalyst as obtained in the above, the reaction was carried out in the same manner with Example 3. The results were as shown in Table 2.

Example 8

Example 6 was repeated except that the carrier was sifted out with a sieve of a mesh size not greater than 9.0 mm and not less than 6.7 mm. The results were as shown in Table 2. The carrier had an average particle size of 8.02 mm, standard deviation of 0.64 and relative standard deviation of 0.08. The resulting oxide catalyst had an average particle size of 8.52 mm, standard deviation of 0.68 and relative standard deviation of 0.08.

Example 9

The carrier as used in Example 7 was sifted out with a sieve of a mesh size not greater than 9.0 mm and not less than 6.7 mm. Otherwise, Example 7 was repeated. The results were as shown in Table 2. The carrier had an average particle size of 8.02 mm, standard deviation of 0.64 and relative standard deviation of 0.08. The resulting oxide catalyst had an average particle size of 8.97 mm, standard deviation of 0.72 and relative standard deviation of 0.08.

Comparative Example 5

Example 6 was repeated except that the carrier was sifted out with a sieve of a mesh size not greater than 8.2 mm and not less than 7.8 mm. The results were as shown in Table 2. The carrier had an average particle size of 8.00 mm, standard deviation of 0.08 and relative standard deviation of 0.01. The resulting oxide catalyst had an average particle size of 8.50 mm, standard deviation of 0.09 and relative standard deviation of 0.01.

Comparative Example 6

Example 7 was repeated except that the carrier was sifted out with a sieve of a mesh size not greater than 8.2 mm and not less than 7.8 mm. The results were as shown in Table 2. The carrier had an average particle size of 8.00 mm, standard deviation of 0.08 and relative standard deviation of 0.01. The resulting oxide catalyst had an average particle size of 8.95 mm, standard deviation of 0.09 and relative standard deviation of 0.01.

TABLE 2

| | Carrier | | Catalyst | | | | | Per-pass | |
| --- | --- | --- | --- | --- | --- | --- | --- | --- | --- |
| | Average particle size (mm) | Relative standard deviation | Average particle size (mm) | Relative standard deviation | Operation Time (hr) | Reaction Temp. (° C.) | Hot Spot Temp. (° C.) | Acrolein Conversion (mol %) | Yield of Acrylic Acid (mol %) |
| Example 3 | 5.00 | 0.05 | 5.16 | 0.04 | initial stage | 267 | 58 | 98.4 | 93.4 |
| | | | | | 2000 | 268 | 57 | 98.4 | 93.4 |
| Example 4 | 4.82 | 0.14 | 5.16 | 0.13 | initial stage | 264 | 60 | 98.4 | 93.5 |
| | | | | | 2000 | 264 | 60 | 98.3 | 93.4 |
| Comparative Example 3 | 4.99 | 0.21 | 5.16 | 0.21 | initial stage | 253 | 94 | 99.5 | 87.1 |
| | | | | | 2000 | 258 | 89 | 98.7 | 85.8 |
| Comparative Example 4 | 5.00 | 0.01 | 5.19 | 0.01 | initial stage | 272 | 51 | 98.3 | 89.0 |
| | | | | | 2000 | 274 | 53 | 97.7 | 87.7 |
| Example 5 | 4.99 | 0.21 | 5.13 | 0.15 | initial stage | 262 | 62 | 98.6 | 93.6 |
| | | | | | 2000 | 262 | 61 | 98.4 | 93.5 |
| Example 6 | 8.00 | 0.04 | 8.50 | 0.04 | initial stage | 275 | 51 | 98.3 | 93.4 |
| | | | | | 2000 | 275 | 51 | 98.2 | 93.4 |
| Example 7 | 8.00 | 0.04 | 8.95 | 0.04 | initial stage | 277 | 50 | 98.6 | 93.6 |
| | | | | | 2000 | 278 | 49 | 98.4 | 93.5 |
| Example 8 | 8.02 | 0.08 | 8.52 | 0.08 | initial stage | 275 | 53 | 98.2 | 93.7 |
| | | | | | 2000 | 275 | 52 | 98.2 | 93.6 |
| Example 9 | 8.02 | 0.08 | 8.97 | 0.08 | initial stage | 275 | 51 | 98.3 | 93.4 |
| | | | | | 2000 | 276 | 51 | 98.3 | 93.4 |
| Comparative Example 5 | 8.00 | 0.01 | 8.50 | 0.01 | initial stage | 286 | 48 | 98.2 | 88.1 |
| | | | | | 2000 | 288 | 47 | 97.9 | 87.9 |
| Comparative Example 6 | 8.00 | 0.01 | 8.95 | 0.01 | initial stage | 288 | 46 | 98.0 | 87.6 |
| | | | | | 2000 | 289 | 45 | 97.8 | 87.5 |

Example 10

-Reaction-

A fixed bed shell-and-tube reactor composed of about 8,500 reaction tubes (each 25 mm in diameter and 5,000 mm in length) and a shell for passing a hot medium, which covered the reaction tubes, was filled with the catalyst obtained in Example 1 ("first stage catalyst"), SUS Raschig rings of each 8 mm in outer diameter, and the catalyst obtained in Example 3 ("second stage catalyst") by successively dropping them from the top of the reaction tubes, to make their respective layer lengths as follows: 2,300 mm for the first stage catalyst, 400 mm for the Raschig rings and 2,300 mm for the second stage catalyst. At the position 2,500 mm from the bottom of the shell, a 50 mm-thick partition plate was provided to divide the shell into the upper and lower parts. In both the upper and lower shell spaces a hot medium was circulated upward. From a bottom part of the reactor, a gaseous mixture composed of 8 vol % of propylene, 76 vol % of air, 12 vol % of steam and the balance of inert gas such as nitrogen was introduced, and the reaction was carried out at a space velocity to the first stage catalyst of 1,600 h$^{-1}$ (STP). The performances at the initial stage of the reaction and after 2,000 hours' reaction were as shown in Table 3.

TABLE 3

| | Operation time (hr) | Reaction temp. at first stage catalyst (° C.) | Hot spot temp. (° C.) | Reaction temp. at second stage catalyst (° C.) | Hot spot temp. (° C.) | Propylene conversion (mol %) | Acrolein Yield (mol %) |
| --- | --- | --- | --- | --- | --- | --- | --- |
| Example 10 | initial stage | 315 | 61 | 270 | 60 | 98.5 | 89.6 |
| | 2000 | 316 | 61 | 271 | 59 | 98.5 | 89.4 |

The invention claimed is:

1. An oxide catalyst containing molybdenum as an essential component, wherein the relative standard deviation of its particle size as determined according to the following formula (1):

$$\text{relative standard deviation of particle size} = \quad (1)$$

standard deviation of particle size/average particle size wherein the standard deviation of particle size =

$$\sqrt{\frac{N\Sigma Xn^2 - (\Sigma Xn)^2}{N(N-1)}}$$

(N is the number of particles whose size is measured; Xn is the size of each particle in terms of triaxial average diameter which is the average value of diameters measured in three directions of each particle); and the average particle size is the arithmetic mean of particle sizes of N particles is at least 0.04 and no more than 0.20, and wherein the oxide catalyst is represented by the following formula (3):

$$Mo_{12}V_gW_hCu_iE_jF_kG_lH_mO_y \quad (3)$$

wherein Mo is molybdenum, V is vanadium, W is tungsten, Cu is copper, E is at least an element selected from cobalt, nickel, iron, lead and bismuth, F is at least an element selected from antimony, niobium and tin, G is at least an element selected from silicon, aluminum, titanium and zirconium, H is at least an element selected from alkali metals, and O is oxygen; g, h, i, j, k, l, m and y are respective atomic ratios of V, W, Cu, E, F, G, H and O, which are, respectively, $2 \leqq g \leqq 15$, $0 \leqq h \leqq 10$, $0 < i \leqq 6$, $o \leqq j \leqq 30$, $0 \leqq k \leqq 6$, $0 \leqq l \leqq 60$, $0 \leqq m \leqq 6$, and y is a numerical value determined by the state of oxidation of respective elements.

2. A supported catalyst formed by supporting the catalyst as described in claim 1 on a carrier.

3. A supported catalyst formed by supporting the catalyst as described in claim 1 on a carrier whose relative standard deviation of particle size as determined according to the formula (1) is not less than 0.04 and not more than 0.20.

* * * * *